United States Patent
Grashow (10) Patent No.: US 10,029,061 B2
(45) Date of Patent: Jul. 24, 2018

(54) METHOD AND DEVICE FOR SIZING MASKS

(71) Applicant: KONINKLIJKE PHILIPS N.V., Eindhoven (NL)

(72) Inventor: Jonathan Sayer Grashow, Cheswick, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 14/787,776

(22) PCT Filed: Apr. 22, 2014

(86) PCT No.: PCT/IB2014/060887
§ 371 (c)(1),
(2) Date: Oct. 29, 2015

(87) PCT Pub. No.: WO2014/177972
PCT Pub. Date: Nov. 6, 2014

(65) Prior Publication Data
US 2016/0067436 A1    Mar. 10, 2016

Related U.S. Application Data (60) Provisional application No. 61/818,656, filed on May 2, 2013.

(51) Int. Cl.
*A61B 5/107* (2006.01)
*A61M 16/06* (2006.01)

(52) U.S. Cl.
CPC ........... *A61M 16/06* (2013.01); *A61B 5/1077* (2013.01); *A61M 2016/0661* (2013.01)

(58) Field of Classification Search
CPC .................................................... A61B 5/1077
USPC ................................................... 33/512, 562
See application file for complete search history.

(56) References Cited

U.S. PATENT DOCUMENTS

| | | | | |
|---|---|---|---|---|
| 4,138,820 A * | 2/1979 | O'Connor | ............... | G01B 3/04 33/199 R |
| 5,584,125 A | 12/1996 | Prete | | |
| 6,904,690 B2 * | 6/2005 | Bakke | ..................... | G01B 3/42 33/1 H |

(Continued)

FOREIGN PATENT DOCUMENTS

| | | |
|---|---|---|
| CN | 2225661 Y | 4/1996 |
| CN | 1750853 A | 3/2006 |

(Continued)

OTHER PUBLICATIONS

Fisher & Paykel: "Multi-Mask Sizing Gauge—Flexifit 432", Internet Citation, 2012, pp. 1, XP00269, Retrieved from the Internet:URL:http://web.archive.org/1iveweb/http://www.cpapxchange.com/cpap-masks-bi pap-masks/flexifit-infinity-cpap-sizing-guide.pdf [retrieved on Jun. 14, 2013].

*Primary Examiner* — G. Bradley Bennett
(74) *Attorney, Agent, or Firm* — Michael W. Haas (57) ABSTRACT

A method of providing a range of different sized masks for fitting to a patient includes providing a first mask having an upper lip engagement surface having a first concavity and a first nasal envelope and providing a second mask having an upper lip engagement surface having a second concavity different than the first concavity and a second nasal envelope.

12 Claims, 12 Drawing Sheets

(56) References Cited

U.S. PATENT DOCUMENTS

| | | |
|---|---|---|
| 7,743,920 B1 | 6/2010 | Lordo |
| 8,028,699 B2 | 10/2011 | Ho |
| 8,042,538 B2 | 10/2011 | Ging |
| 8,776,387 B1 * | 7/2014 | Butler-Ammar ..... A61J 11/0035 33/512 |
| 2002/0095810 A1 * | 7/2002 | Carlson ................. B26B 29/06 33/562 |
| 2006/0136069 A1 * | 6/2006 | Francalacci Franca .. A61F 2/12 623/23.67 |
| 2009/0194107 A1 | 8/2009 | Loeser |
| 2011/0162654 A1 | 7/2011 | Carroll |
| 2011/0232646 A1 | 9/2011 | Ho |
| 2011/0247623 A1 | 10/2011 | McCarthy |
| 2014/0182151 A1 * | 7/2014 | Li ......................... A45D 29/00 33/512 |
| 2016/0354567 A1 * | 12/2016 | Grashow ............. A61M 16/161 |

FOREIGN PATENT DOCUMENTS

| | | |
|---|---|---|
| CN | 2845755 Y | 12/2006 |
| WO | WO2010135785 A1 | 12/2010 |

\* cited by examiner

METHOD AND DEVICE FOR SIZING MASKS

CROSS-REFERENCE TO RELATED APPLICATIONS

This patent application claims the priority benefit under 35 U.S.C. § 371 of international patent application no. PCT/IB2014/060887, filed Apr. 22, 2014, which claims the priority benefit under 35 U.S.C. § 119(e) of U.S. Provisional Application No. 61/818,656 filed on May 2, 2013, the contents of which are herein incorporated by reference.

BACKGROUND OF THE INVENTION

1. Field of the Invention

The present invention pertains generally to methods for sizing masks, and, more particularly, to a method for sizing a mask used to treat a patient who suffers from disordered breathing. The present invention also relates to devices used in sizing such masks and methods for providing such masks.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint the patient's airway open, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal/oral mask that covers the patient's nose and mouth, a nasal mask that covers the patient's nose, a nasal cushion that rests beneath the patient's nose (such as a "pillows" style nasal cushion having nasal prongs that are received within the patient's nares or a "cradle" style nasal cushion that rests beneath and covers the patient's nares), or a full face mask that covers the patient's face.

Traditionally masks used for respiratory therapy are generally sized such that the length, width, and/or depth of one size of a given mask accommodates a prescribed subpopulation of users, and a set of such sizes (which vary in length, width, and/or depth) are developed such that the corresponding facial geometry of almost any user among the entire population of users is accommodated by at least one size of mask from the set.

Figure 1:
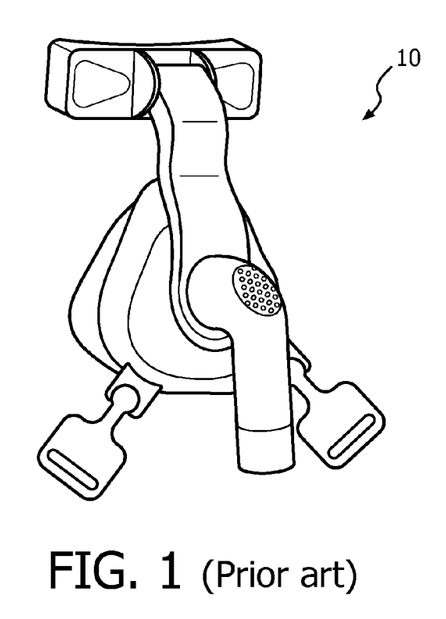
FIG. 1 is a front isometric view of an example known nasal mask.
Figure 2:
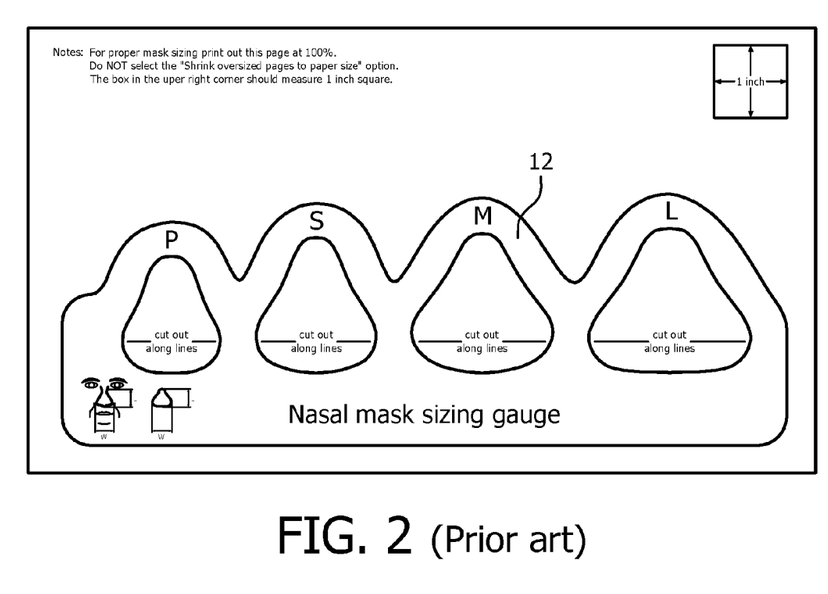
FIG. 2 is a plan view of an example known sizing gauge for sizing a nasal mask such as shown in FIG. 1 for a patient.

As an example, sizing for a nasal mask, such as the example mask 10 shown in FIG. 1, has traditionally been accomplished by increasing the length L and (in some cases) the width W as the sizes progress from the smallest to the largest, such as shown by the sizing gauge 12 of FIG. 2, while the depth D (FIG. 6) is held constant such that the nasal protrusion of any user is accommodated by every size in the set.

Figure 3:
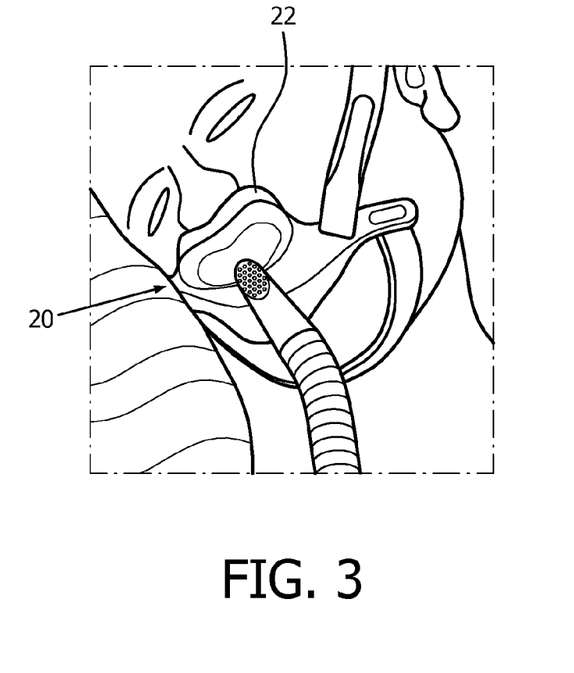
FIG. 3 is an isometric view of an example known cradle mask shown disposed on the head of a patient.
Figure 4:
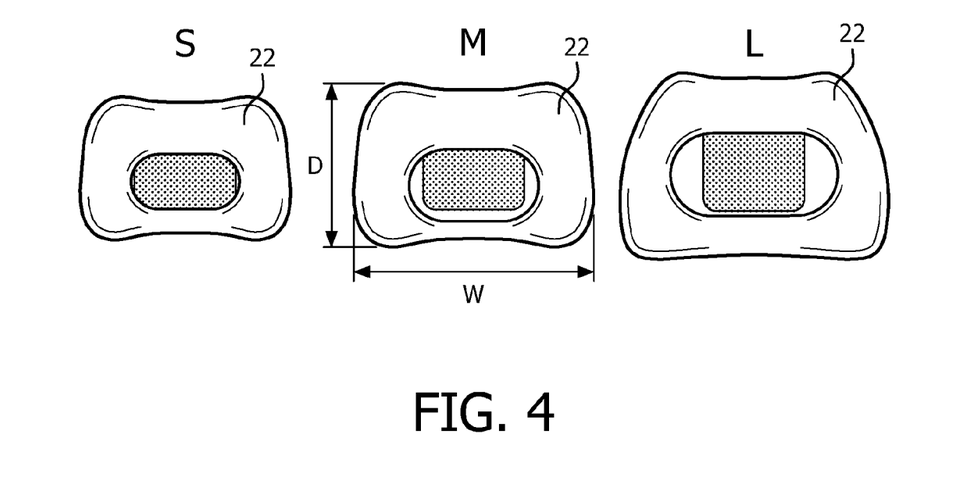
FIG. 4 is a top view of three example know cushions of varying size for use with the cradle mask of FIG. 3.

As another example, sizing for a cradle mask, such as the example mask 20 shown in FIG. 3, has traditionally been accomplished by increasing the width W and/or depth D of a cushion 22 as the sizes increase from the smallest to the largest. FIG. 4 shows example top views of small S, medium M and large L versions of cushion 22. Variations in length (i.e., the dimension into the page of FIG. 4) are not typically applicable to this style of cushion since it sits under the nose of a patient and does not engage with the nasal bone.

SUMMARY OF THE INVENTION

In accordance with one aspect of the present invention, a sizing gauge for use in determining the appropriate size mask for a patient is provided. The sizing gauge comprises: a body portion and a number of concave shaped portions of varying depth extending inward from a periphery of the body portion.

The body portion may be generally planar in shape. The number of concave portions may comprise a plurality of concave portion portions, each having a different concavity than the other concave portions, and wherein each concave portion may be adapted to generally engage a patient slightly below the nose in a manner such that a mask sized for a similar upper lip protrusion can readily be identified. The body portion may further include a number of indicia, each being associated with a respective concave portion of the number of concave portions and providing an indication of the mask size corresponding to the respective concave portion. The sizing gauge may be adapted to measure the nasal envelope of a patient. The number of concave portions may comprise a plurality of concave portions, each having a different depth than the other concave portions, and wherein each concave portion is adapted to generally engage a patient generally at and about the tip of the patient's nose in a manner such that a mask sized for a correspondingly sized nasal envelope can readily be identified. The body portion may further includes at least one of: a number of boundary indicators, each being associated with a corresponding one of the number of concave shaped portions and indicative of a nasal envelope of a correspondingly sized mask; or a number cushion airflow apertures, each being associated with a corresponding one of the number of concave shaped portions.

In accordance with another aspect of the present invention, a method for sizing a mask to a patient is provided. The method comprises determining a measurement of one of the upper lip protrusion or nasal envelope of the patient and determining an appropriate sized mask for the patient based on said measurement.

Determining a measurement of one of the upper lip protrusion or nasal envelope of the patient may comprise using a sizing gauge to determine such measurement.

In accordance with yet another aspect of the present invention, a method of providing a range of different sized masks for fitting to a patient is provided. The method comprises: providing a first mask having an upper lip engagement surface having a first concavity and a first nasal envelope; and providing a second mask having an upper lip engagement surface having a second concavity and a second nasal envelope, wherein the second concavity is different than the first concavity.

The first nasal envelope and the second nasal envelope may be generally equal. The second concavity may be greater than the first concavity and the second nasal envelope may be greater than the first nasal envelope.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein. As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

Figure 5:
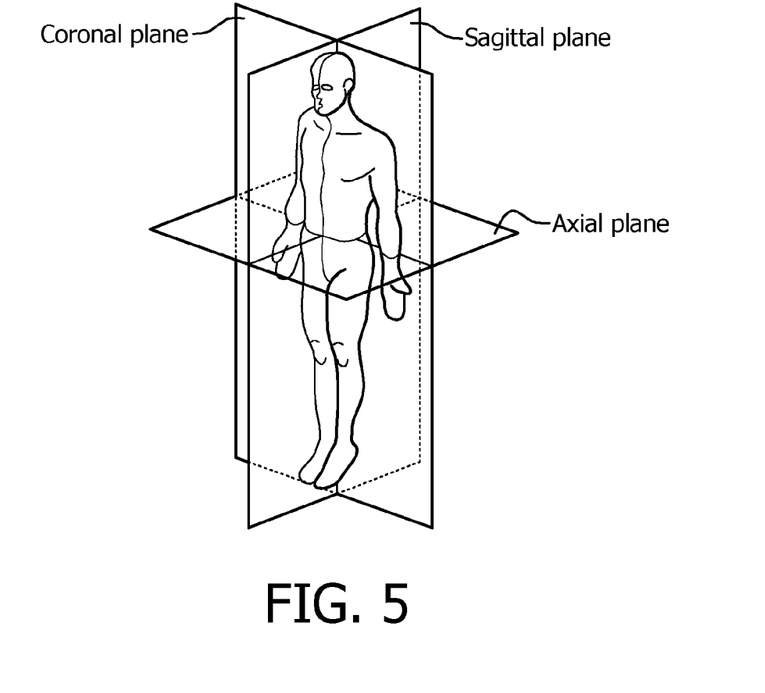
FIG. 5 is an illustration showing the primary reference planes of a human body.
Figure 6:
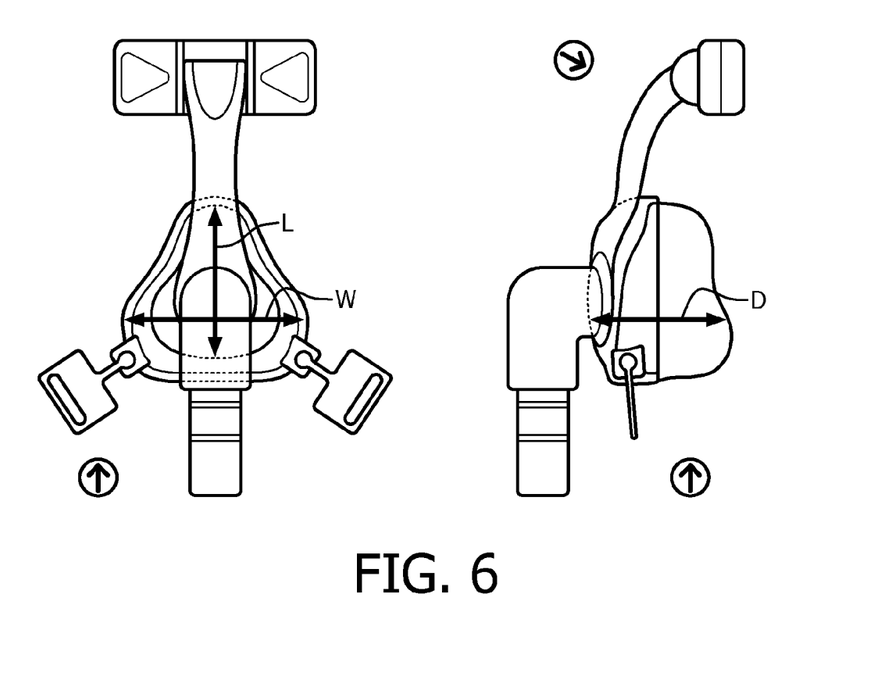
FIG. 6 is front and side views of a known nasal mask identifying the reference dimensions of length, width and depth.

As employed herein, the term "length" shall refer to the dimension of a mask designed to accommodate the distance between the upper lip and the nose bridge or nasal bone, orthogonal to the Axial plane of the body as depicted in FIGS. 5 and 6.

As employed herein, the term "width" shall refer to the dimension of a mask designed to accommodate the distance between the left and right alare of the nose, orthogonal to the sagittal plane of the body as depicted in FIGS. 5 and 6.

As employed herein, the term "depth" shall refer to the dimension of a mask designed to accommodate the protrusion of the nose from the surface of the face, orthogonal to the coronal plane of the body as depicted in FIGS. 5 and 6.

Figure 7:
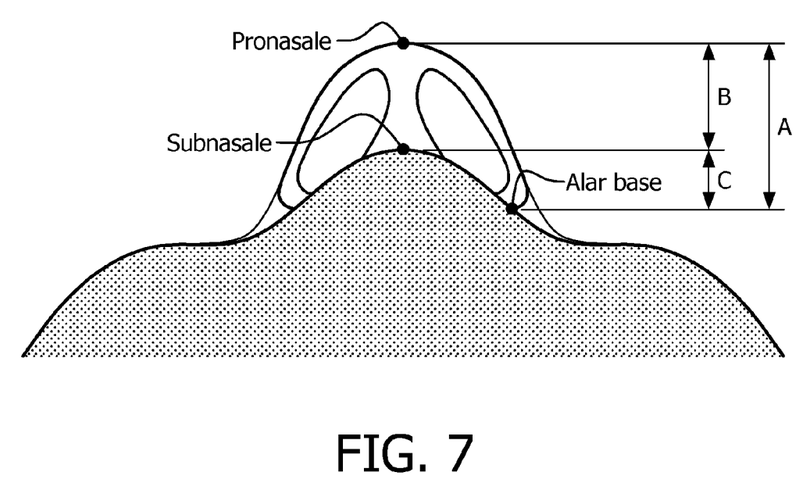
FIG. 7 is an upward view of a patient's face showing the relative positioning of a number of facial landmarks.

As employed herein, the term "nasal protrusion" shall refer to the distance between the subnasale and pronasale, orthogonal to the sagittal plane of the body, such as shown by element "B" of FIG. 7.

As employed herein, the term "upper lip protrusion" shall refer to the distance between the alar base and the subnasale, orthogonal to the sagittal plane of the body, such as shown by element "C" in FIG. 7. Upper lip protrusion C is generally defined by the curvature of the maxilla bone.

As employed herein, the term "nasal envelope" shall refer to the distance between the alar base and the pronasale, orthogonal to the sagittal plane of the body (i.e., nasal envelope=nasal protrusion+upper lip protrusion), such as shown by element A of FIG. 7.

Embodiments of the present invention improve upon conventional sizing schemata for both nasal and cradle masks which fail to accommodate variations in upper lip protrusion. This failure commonly results in uncomfortable pressure on the upper lip and/or septum of a patient as well as leaks proximal to the upper lip and alar base. This issue becomes even more pronounced for masks that seal against the top of the upper lip such as cradle cushions or small footprint nasal masks.

Additionally, the conventional sizing schema for some nasal masks assigns a single depth D for all sizes of a given mask. This results in a mask with a large standoff from the face even for users with a relatively small nasal protrusion. This large standoff affects the stability of the mask when subjected to external forces (e.g. a pillow, bedding, gravity) and also partially blocks the field of vision for some patients. Embodiments of the present invention solve these problems (among others) by providing a sizing schema that accommodates variability in upper lip protrusion and optionally variability in nasal envelope.

Figure 8:
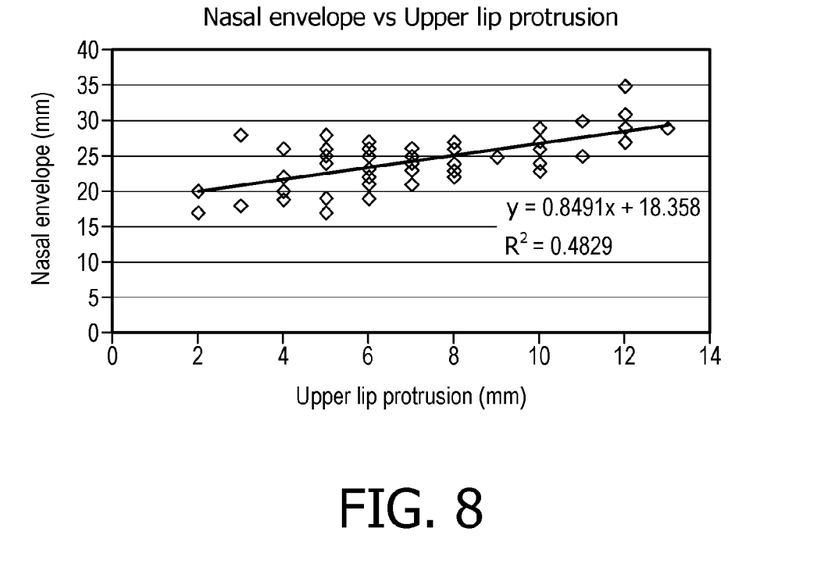
FIG. 8 is an X-Y scatter plot showing the relationship of the length of Nasal Envelope versus Upper Lip Protrusion amongst a population sampling.
Figure 9:
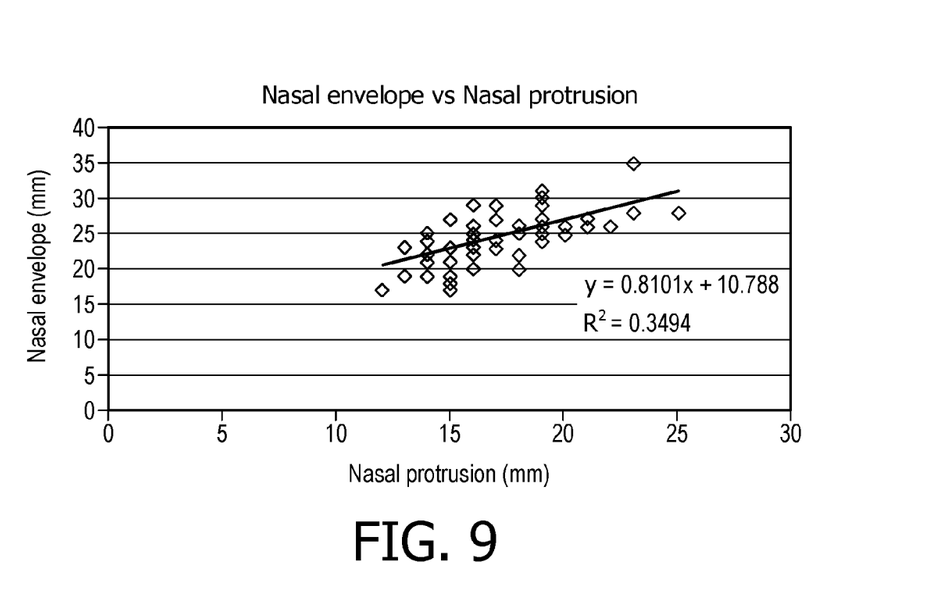
FIG. 9 is an X-Y scatter plot showing the relationship of the length of Nasal Envelope versus Nasal Protrusion amongst a population sampling.

Referring to the scatter plots of FIGS. 8 and 9, in-house anthropometric analysis has revealed that upper lip protrusion varies significantly among the population. The results of an internal study showed that the standard deviation of upper lip protrusion (7.5±3.6 mm) was actually greater than nasal protrusion (17.2±2.7 mm). Such findings indicate that accommodation of variability in upper lip protrusion is critical for a mask sizing schema. Furthermore, the results of the same internal study showed that variability in the nasal envelope was more strongly correlated with upper lip protrusion (FIG. 8) than with nasal protrusion (FIG. 9), thus indicating that by progressively increasing the overall cushion depth concurrently with the concavity of the upper lip engagement surface a more effective sizing strategy may be obtained.

Figure 10:
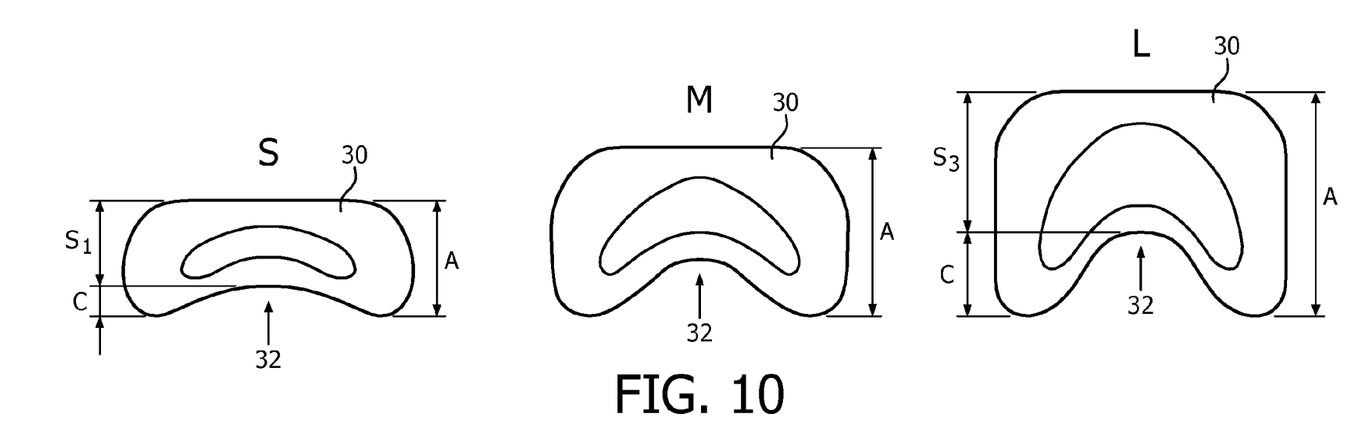
FIG. 10 is an example of a plurality of cradle cushions of varying sizes shown schematically in accordance with an example embodiment of the present invention.

Referring to FIG. 10, in one example embodiment of a sizing schema for a cradle cushion 30 in accordance with the present invention, the degree of concavity (i.e., the amount of upper lip protrusion C) of the upper lip engagement surface 32 increases progressively as the size of cushion 30 increases, such as shown by the top view of the example small S, medium M, and Large L cushions 30. In this embodiment the nasal envelope A of a cushion 30 increases proportionally with the concavity of the upper lip engagement surface 32 such that the smaller size S cushion 30 has a lesser standoff S from the face compared to the standoff $S_3$ of the larger size L cushion 30. The following table gives an example of dimensions of such an embodiment:

TABLE 1

| Size | Nasal Envelope A (mm) | Upper Lip Protrusion C (mm) |
| --- | --- | --- |
| Small | 15-23 | 0-10 |
| Medium | 24-27 | 4-12 |
| Large | 28-35 | 5-13 |

Figure 11:
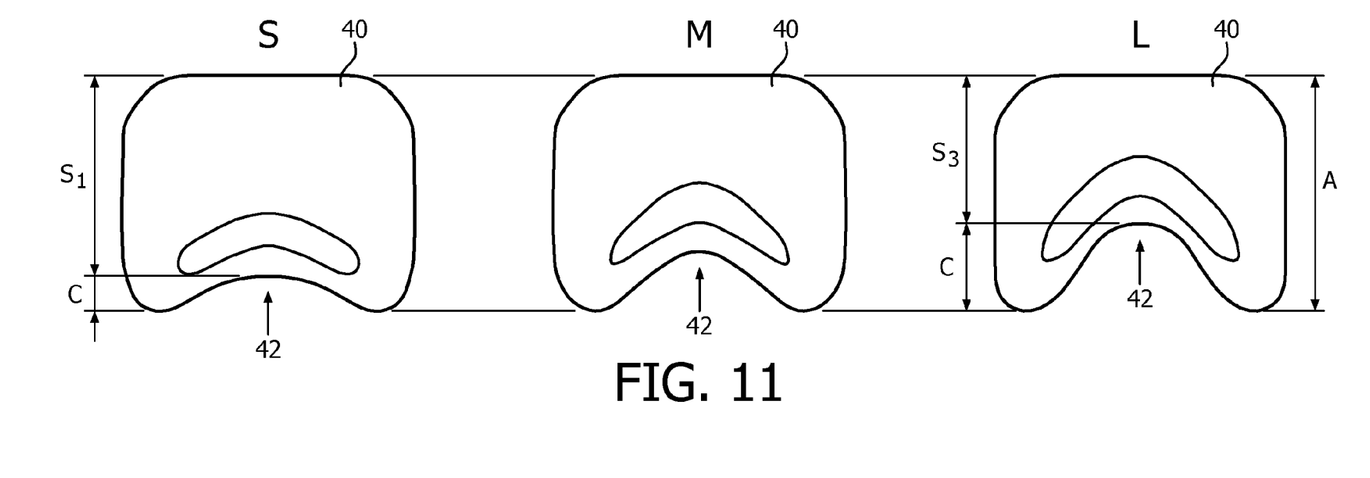
FIG. 11 is an example of a plurality of cradle cushions of varying sizes in accordance with another example embodiment of the present invention.

Referring to FIG. 11, in another example embodiment of a sizing schema for a cradle cushion 40 in accordance with the present invention, the degree of concavity (i.e., the amount of upper lip protrusion C) of the upper lip engagement surface 42 increases progressively as the size of the cushion increases (moving from S to L), but unlike the previous embodiment described in conjunction with FIG. 10 in which the nasal envelope A increased with increasing cushion size, the nasal envelope A of each cushion 40 is constant across all of the sizes S-L. An advantage of this embodiment as compared to the previous embodiment is that it may provide a functional seal for more users since upper lip protrusion and nasal envelope may not be perfectly correlated. This functional advantage comes at the expense of increased standoff (see $S_1$ vs. $S_3$ in FIG. 11) from the face for the smaller sizes.

Figure 12:
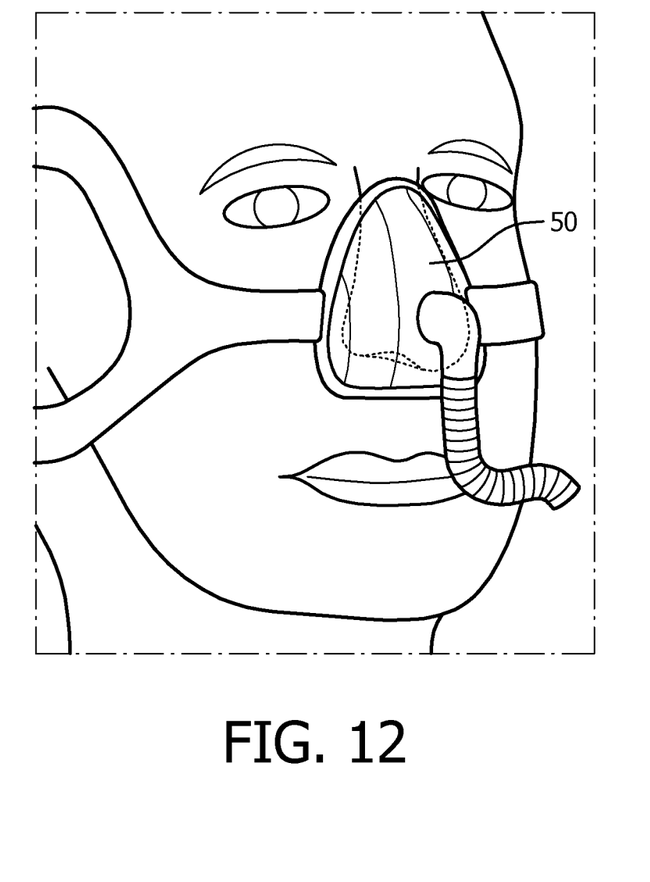
FIG. 12 is an isometric view of a low profile nasal cushion in accordance with another example embodiment of the present invention shown disposed on the face of a patient.
Figure 13:
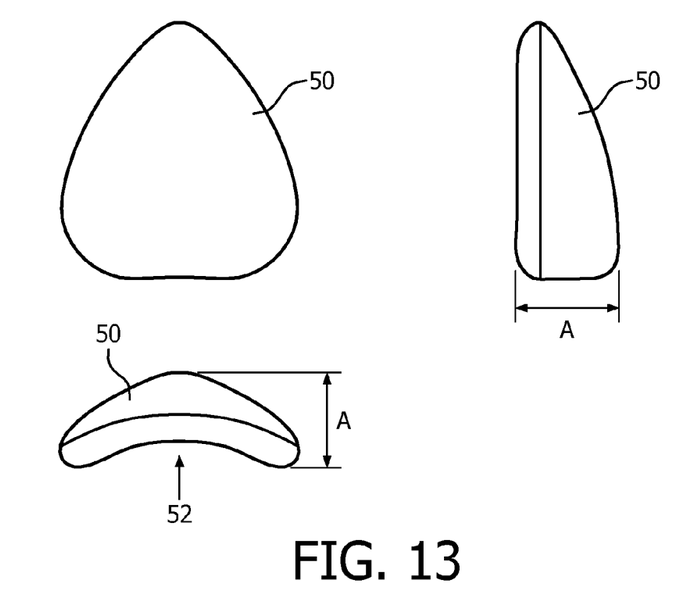
FIG. 13 is front, side and bottom views of the low profile nasal cushion of FIG. 12.
Figure 14:
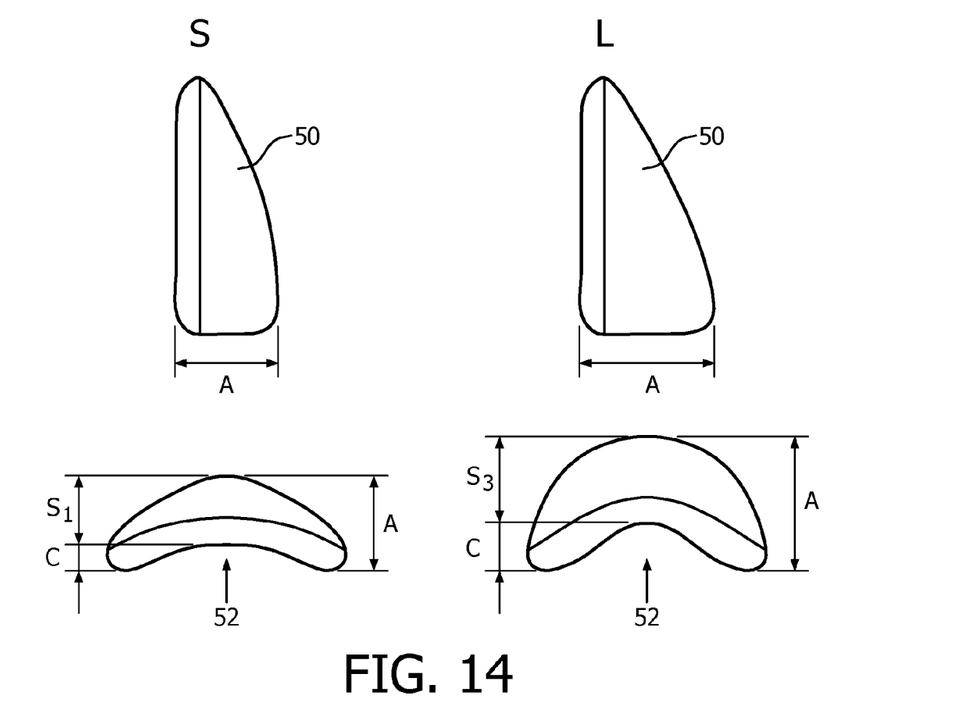
FIG. 14 is side and bottom views of small and large size versions of the nasal cushion of FIG. 12.

Referring to FIGS. 12-14, in an example embodiment of a sizing schema for a low profile nasal cushion 50, the degree of concavity of the upper lip engagement surface 52 (i.e., the amount of upper lip protrusion C) increases progressively as the size of cushion 50 increases and the nasal envelope A of the cushion 50 increases proportionally with the concavity of the upper lip engagement surface 52 such that the smaller size S has a decreased standoff $S_1$ from the face compared to the standoff $S_3$ of the larger size L (FIGS. 13, 14).

Figure 15A:
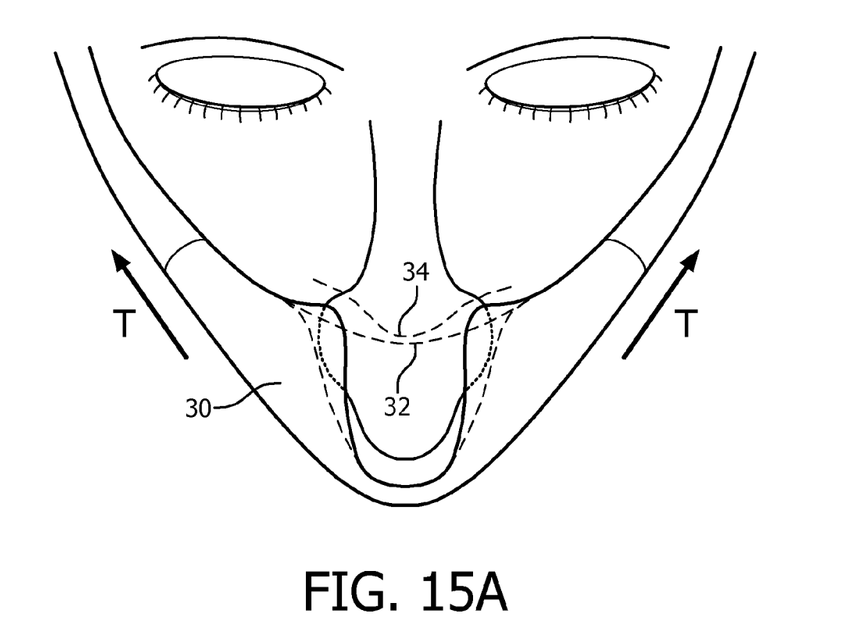
FIG. 15A is a top view of a cushion in accordance with an example embodiment of the present invention shown loosely disposed on the face of a patient.
Figure 15B:
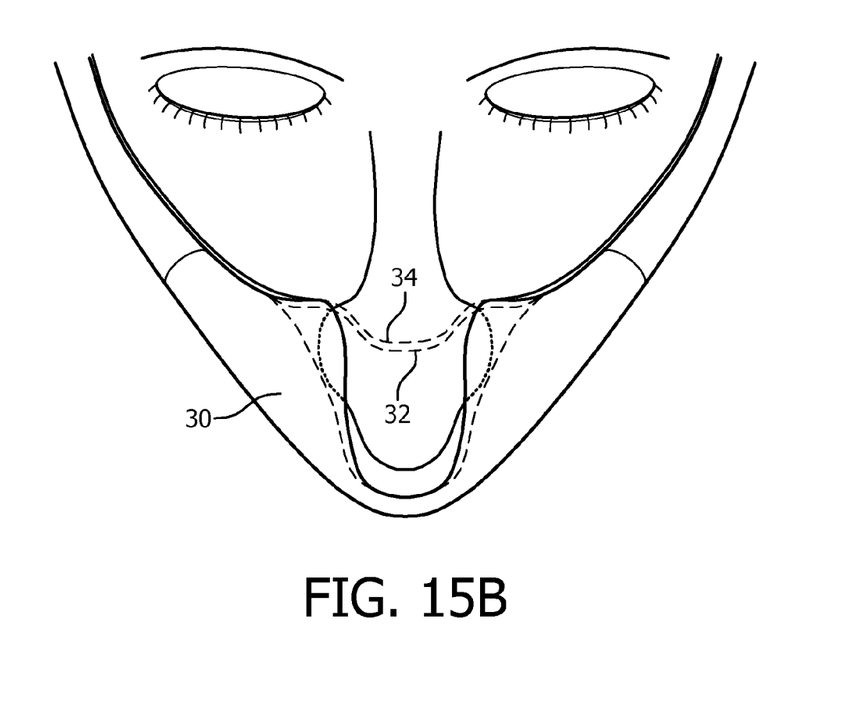
FIG. 15B is a top view of the cushion of FIG. 15A shown tightened on the face of a patient.

As can be seen in the cradle mask embodiment previously discussed in regard to FIG. 10, it may be necessary for each size cushion (S, M, L) to accommodate a range of upper lip protrusions. The present invention contemplates three potential strategies to address this need. As one approach, such as shown in FIG. 15A, the upper lip engagement surface 32 of the cushion 30 may be designed to match the contour of the smallest upper lip protrusion intended to be fit with each size. The mask is then constructed to allow the upper lip engagement surface 32 to be compressed (see FIG. 15B), and thus made to conform to the patient's upper lip 34 without putting undue force on the upper lip when the headgear is tightened on the patient in a direction T (FIG. 15A).

Figure 16A:
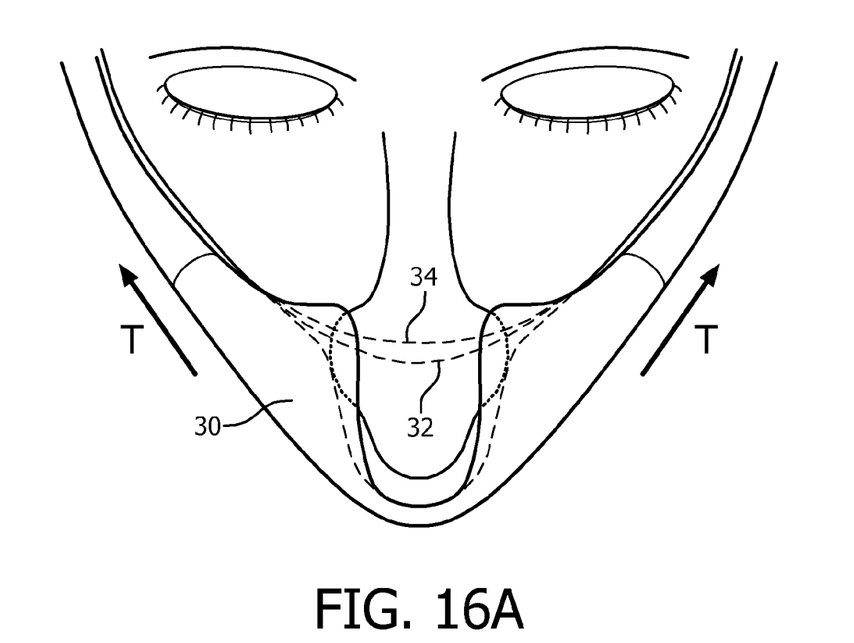
FIG. 16A is a top view of a cushion in accordance with another example embodiment of the present invention shown loosely disposed on the dace of a patient.
Figure 16B:
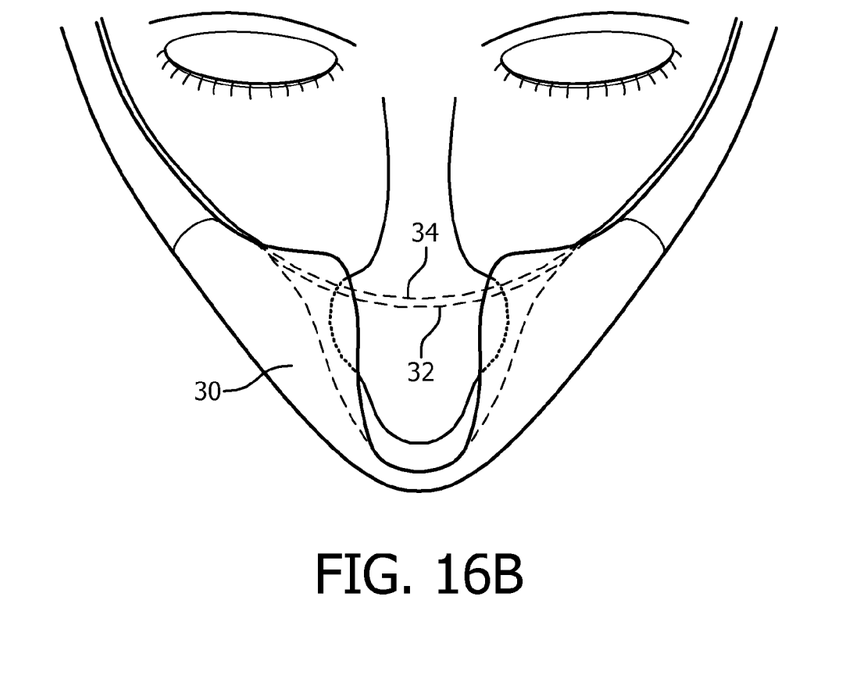
FIG. 16B is a top view of the cushion of FIG. 16A shown tightened on the face of a patient.

As another approach, such as illustrated in FIGS. 16A and 16B, the upper lip engagement surface 32 of the mask 30 may be sized to match the contour of the largest upper lip protrusion intended to be fit with each size. The mask is then constructed to allow the upper lip engagement surface 32 to become flattened, and thus made to conform to the patient's upper lip 34, the headgear is tightened on the patient in a direction T (FIG. 16A).

As yet another approach, the upper lip engagement surface 30 of the mask 32 may be designed to match a contour somewhere between the largest and smallest upper lip protrusions intended to be fit with each size (e.g. the midpoint). The mask is then constructed to allow the mechanisms from both of the previously discussed approaches to be employed depending on the specific geometry of the wearer.

Having thus described the general dimensioning of different sized masks/cushions in accordance with the present invention, methods of selecting the appropriate sized mask for a particular patient will now be discussed. In order to determine the proper mask size for a patient it is sometimes advantageous to use a sizing gauge which prevents the wearer from needing to try on several different masks to find the optimal size. Three examples of gauges in accordance with the present invention that could be used for the above-mentioned embodiments are illustrated in FIGS. 17-19.

Figure 17:
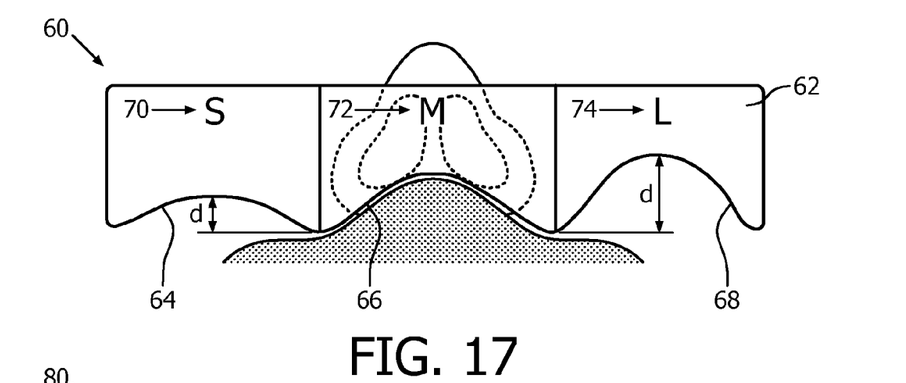
FIGS. 17-19 are plan views of sizing gauges in accordance with example embodiments of the present invention.

FIG. 17 illustrates a sizing gauge 60 for measuring the upper lip protrusion C of a patient and could be used in selecting the appropriate size mask/cushion from any of the embodiments previously described herein. Sizing gauge 60 includes a generally planar body 62 and a number (three are included in the illustrated embodiment) of concave shaped portions 64, 66, and 68 of varying depth d extending inward from an edge of body 62. Each concave portion is of different concavity than the other concave portions and is adapted to generally engage a patient slightly below the nose (and above the upper lip) in a manner such that a mask sized for a similar upper lip protrusion C (FIG. 7) can readily be identified. In order to assist in such identification of a correspondingly sized mask, each portion 64, 66, 68 may have an indicia 70, 72, 74 associated therewith that identifies the mask size corresponding to each portion 64, 66, 68. Although the example embodiment illustrated in FIG. 17 includes three portions labeled S, M and L, it is to be appreciated that one or more of the quantity, relative positioning (along the same, or different sides of body 62), and/or the indicia associated with such portions may be varied without varying from the scope of the present invention.

Figure 18:
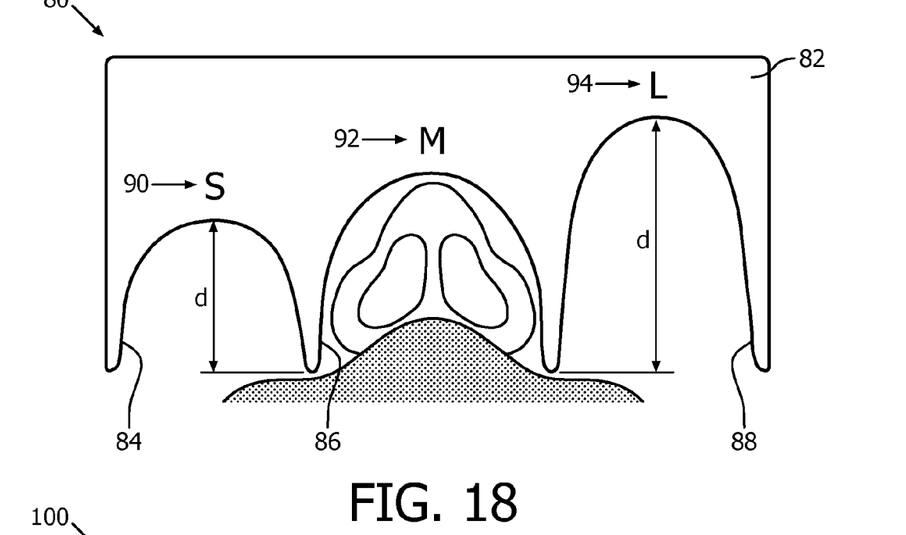

FIG. 18 illustrates an example sizing gauge 80 for measuring the nasal envelope of a patient and could be used with a sizing scheme which assumes a correlation between nasal envelope A and upper lip protrusion C. Sizing gauge 80 includes a generally planar body 82 and a number (three are included in the illustrated embodiment) of concave shaped portions 84, 86, and 88 of varying depth d extending inward from an edge of body 82. Each concave portion is of a different depth d than the other concave portions and is adapted to generally engage a patient generally at and about the tip of the patient's nose in a manner such that a mask sized for a nasal envelope can readily be identified. In order to assist in such identification of a correspondingly sized mask, each portion 84, 86, 88 may have an indicia 90, 92, 94 associated therewith that identifies the mask size corresponding to each portion 84, 86, 88. Although the example embodiment illustrated in FIG. 18 includes three portions labeled S, M and L, it is to be appreciated that one or more of the quantity, relative positioning (along the same, or different sides of body 82), and/or the indicia associated with such portions may be varied without varying from the scope of the present invention.

Figure 19:
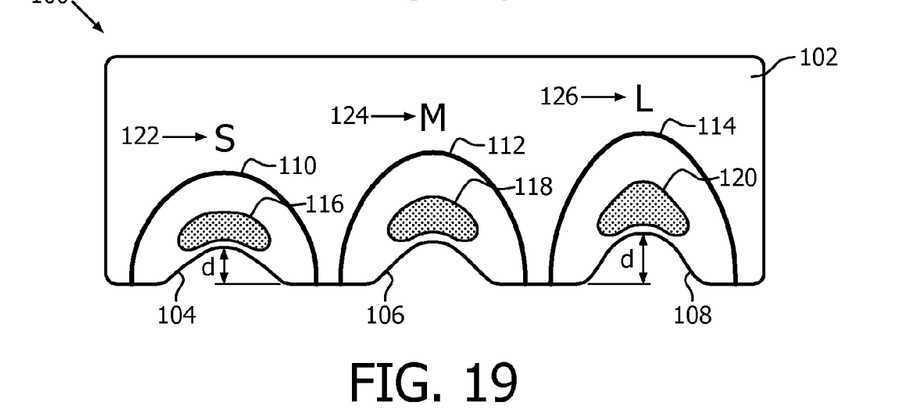

FIG. 19 illustrates an example sizing gauge 100 which combines the functionality of the gauges shown in FIGS. 17 and 18 and provides additional functionality. Sizing gauge 100 includes a generally planar body 102 which, similar to sizing gauge 60 illustrated in FIG. 17, includes a number (three are included in the illustrated embodiment) of concave shaped portions 104, 106 and 108 of varying depth d extending inward from an edge of body 102 for measuring the upper lip protrusion C (FIG. 7) of a patient in a similar manner as previously discussed in regard to sizing gauge 60. Sizing gauge 100 further includes a corresponding number (three are included in the illustrated embodiment) of boundary indicators 110, 112 and 114, each associated with a corresponding one of concave shaped portions 104, 106 and 108. Each of boundary indicators 110, 112 and 114 is indicative of the nasal envelope A (FIG. 7) of a correspondingly size mask/cushion.

In addition to providing for measurement of both the upper lip protrusion and nasal envelope of a patient, sizing gauge 100 also includes a number cushion airflow apertures 116, 118 and 120 (each being associated with a respective concave shaped portion and a boundary indicator) for observing coverage of a patient's nose with respect thereto. Similar to sizing gages 60 and 80, sizing gage 100 may also include indicia 122, 124, 126 associated with portions 104, 106 and 108 in order to assist in identification of a correspondingly sized mask. Although the example embodiment illustrated in FIG. 19 includes three portions labeled S, M and L, it is to be appreciated that one or more of the quantity, relative positioning (along the same, or different sides of body 102), and/or the indicia associated with such portions may be varied without varying from the scope of the present invention.

In use, the best fitting concave shaped portion 104, 106 or 108 would be fit to the upper lip of a patient. Once the appropriate sized concave shaped portion is determined, fitting of the patient's nose within the related boundary indicator and coverage of the related airflow aperture can then be verified in order to ensure an appropriate fitment.

Figure 20:
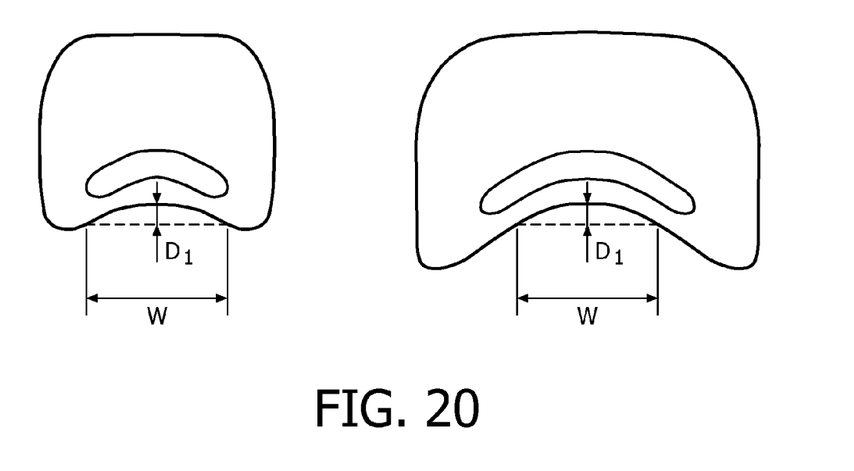
FIGS. 20 and 21 are schematic illustrations of comparative masks in accordance with embodiments of the present invention.
Figure 21:
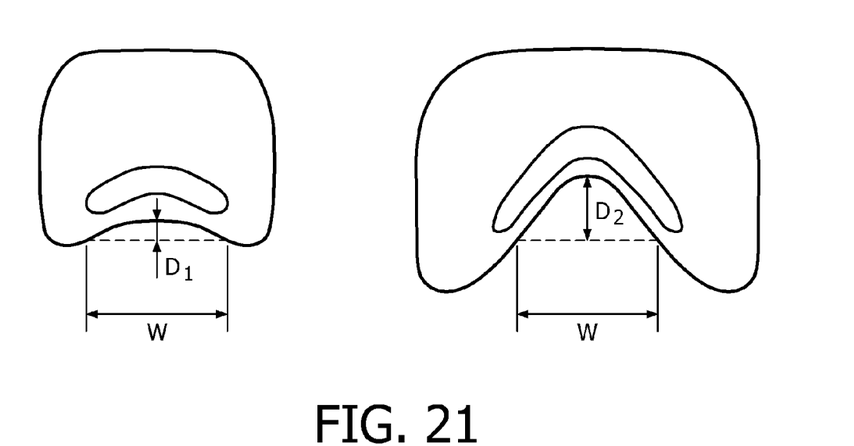

Referring to FIGS. 20 and 21, It is important to note that relative changes in upper lip protrusion between different sizes must be evaluated at the same width. If a mask is designed to (at least roughly) follow the contour of the upper lip, then the concave upper lip engagement may become deeper if the width of one size of mask is larger than another simply due to the round nature of a typical face (FIG. 20). The application of the present invention requires that the concave upper lip engagement become deeper when evaluated with respect to the datum created by a line which intersects the upper lip engagement at a common width W (FIG. 21).

Although embodiments of the present invention have been generally described herein in conjunction with cradle masks and low profile nasal masks, it is to be appreciated that the concepts described herein may also be applied to other nasal masks, full face masks with upper lip engagement, pillows/cannula masks, and oral masks without varying from the scope of the present invention.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. As an example, although not particularly described herein, it is to be appreciated that the present invention may also be applied to masks which are designed to not engage the upper lip, but rather are designed to cover the nostril openings of a patient while avoiding contact with the upper lip, e.g., without limitation, the "mini-nasal mask" described in U.S. Publication 2009/0194107 A1. This sizing schemes described herein would apply to this type of mask as well even though it does not physically engage with the upper lip since the geometry of the edge of the mask closest to the upper lip still depends on the upper lip protrusion.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

It can be appreciated that while traditional sizing methods have generally served to identify a mask that can be made to work on a particular patient, such masks commonly require particular strapping and other fitments in order to achieve the best fit to the patient, which may still be less than optimal. Accordingly, a need exists for an improved method of sizing masks and/or cushions for a patient which overcomes these and other problems associated with known methods.

What is claimed is:

1. A sizing gauge for use in determining the appropriate size mask for a patient, the sizing gauge comprising:
   a body portion; and
   a number of concave shaped portions of varying depth extending inward from a periphery of the body portion.

2. The sizing gauge of claim 1 wherein the body portion is generally planar in shape.

3. The sizing gauge of claim 1 wherein the number of concave portions comprises a plurality of concave portion portions, each having a different concavity than the other concave portions, and wherein each concave portion is adapted to generally engage a patient slightly below the nose in a manner such that a mask sized for a similar upper lip protrusion can readily be identified.

4. The sizing gauge of claim 1 wherein the body portion further includes a number of indicia, each being associated with a respective concave portion of the number of concave portions and providing an indication of the mask size corresponding to the respective concave portion.

5. The sizing gauge of claim 1 wherein the sizing gauge is adapted to measuring the nasal envelope of a patient.

6. The sizing gauge of claim 1 wherein the number of concave portions comprises a plurality of concave portions each having a different depth than the other concave portions, and wherein each concave portion is adapted to generally engage a patient generally at and about the tip of the patient's nose in a manner such that a mask having a correspondingly sized nasal envelope can readily be identified.

7. The sizing gage of claim 3 wherein the body portion further includes at least one of:
    a number of boundary indicators, each being associated with a corresponding one of the number of concave shaped portions and indicative of a nasal envelope of a correspondingly sized mask; or
    a number cushion airflow apertures, each being associated with a corresponding one of the number of concave shaped portions.

8. A method for sizing a mask to a patient, the method comprising:
    determining a measurement of one of the upper lip protrusion or nasal envelope of the patient; and
    determining an appropriate sized mask for the patient based on said measurement.

9. The method of claim 8 wherein determining a measurement of one of the upper lip protrusion or nasal envelope of the patient comprises using a sizing gauge to determine such measurement.

10. A method of providing a range of different sized masks for fitting to a patient, the method comprising:
    providing a first mask having an upper lip engagement surface having a first concavity and a first nasal envelope; and
    providing a second mask having an upper lip engagement surface having a second concavity and a second nasal envelope, wherein the second concavity is different than the first concavity.

11. The method of claim 10 wherein the first nasal envelope and the second nasal envelope are generally equal.

12. The method of claim 10 wherein the second concavity is greater than the first concavity and wherein the second nasal envelope is greater than the first nasal envelope.

* * * * *